United States Patent [19]

Debono

[11] 4,289,692
[45] Sep. 15, 1981

[54] DERIVATIVES OF A-30912D NUCLEUS

[75] Inventor: Manuel Debono, Indianapolis, Ind.

[73] Assignee: Eli Lilly and Company, Indianapolis, Ind.

[21] Appl. No.: 181,035

[22] Filed: Aug. 25, 1980

Related U.S. Application Data

[63] Continuation-in-part of Ser. No. 103,019, Dec. 13, 1979.

[51] Int. Cl.³ .......................................... C07C 103/52
[52] U.S. Cl. ............................................. 260/112.5 R
[58] Field of Search ................................. 260/112.5 R

[56] References Cited

U.S. PATENT DOCUMENTS

| | | | |
|---|---|---|---|
| 3,150,059 | 9/1964 | Kleinschmidt et al. | 260/112.5 R |
| 3,978,210 | 8/1976 | Mizuno et al. | 260/112.5 R |
| 4,024,245 | 5/1977 | Hoehn et al. | 260/112.5 R |
| 4,024,246 | 5/1977 | Higgins et al. | 260/112.5 R |
| 4,050,989 | 9/1977 | Kuwana et al. | 260/112.5 R |
| 4,173,629 | 11/1979 | Dreyfuss et al. | 260/112.5 R |

FOREIGN PATENT DOCUMENTS

| | | | |
|---|---|---|---|
| 568386 | 4/1972 | Belgium | 260/112.5 R |
| 834289 | 10/1974 | Belgium | 260/112.5 R |
| 859067 | 2/1977 | Belgium | 260/112.5 R |
| 866095 | 4/1977 | Belgium | 112.5 R/ |
| 851310 | 8/1977 | Belgium | 260/112.5 R |

OTHER PUBLICATIONS

The Journal of Antibiotics, vol. 29, No. 12, 1339–1340, 1976.
Agr. Biol. Chem., 37 (11), 2455–2463, 1973.
Agr. Biol. Chem., 37 (12), 2709–2717, 1973.
Agr. Biol. Chem., 38 (3), 521–529, 1974.
Agr. Biol. Chem., 38 (10), 1767–1777 (1974).
The Journal of Biochemistry, vol. 56, No. 4, 1964, 335–343.
The Journal of Antibiotics, vol. 31, No. 4, 373–374 (1978).
The Journal of Antibiotics (1975) 764–769, vol. 28, No. 10.
The Journal of Antibiotics 1976, 380–389, vol. 29, No. 4.
The Journal of Antibiotics 1976, 1268–1274, vol. 29, No. 12.
The Journal of Antibiotics, vol. 29, No. 12, 1275–1280, 1976.
Helvetica Chimica Acta, vol. 57, Fasc. 8 (1974), 2459–2477.
Tetrahedron Letters No. 46, 4147–4150, 1976.
Helvetica Chimica Acta, vol. 62, Fasc. 4 (1979), 1252–1266.

*Primary Examiner*—Delbert R. Phillips
*Attorney, Agent, or Firm*—Nancy J. Harrison; Arthur R. Whale

[57] ABSTRACT

Compounds of the formula

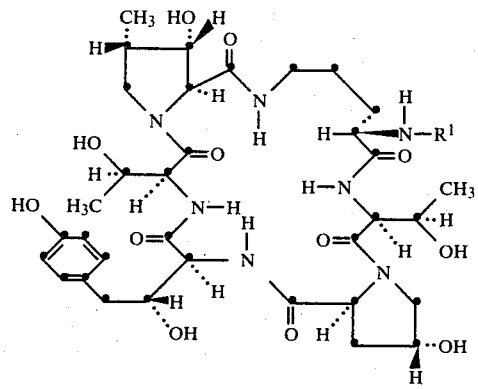

wherein $R^1$ is a group of the formula:

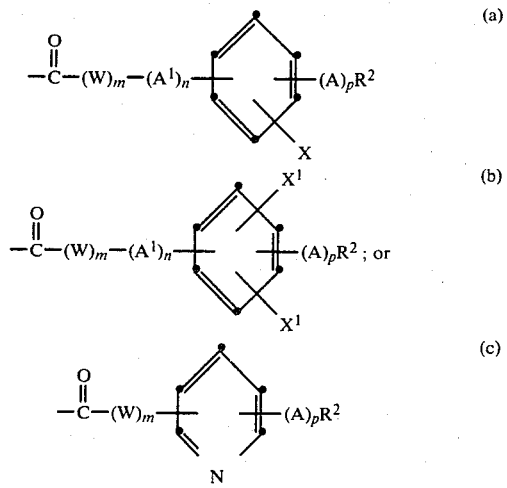

wherein A is divalent oxygen, sulfur, sulfinyl, or sulfonyl; $A^1$ is divalent oxygen, sulfur, sulfinyl, sulfonyl or —NH—; X is hydrogen, chloro, bromo, iodo, nitro, $C_1$–$C_3$ alkyl, hydroxy, $C_1$–$C_3$ alkoxy, mercapto, $C_1$–$C_3$ alkylthio, carbamyl or $C_1$–$C_3$ alkylcarbamyl; $X^1$ is chloro, bromo or iodo; $R^2$ is hydrogen, $C_1$–$C_{18}$ alkyl or $C_2$–$C_{18}$ alkenyl; W is $C_1$–$C_{10}$ alkylene or $C_2$–$C_{10}$ alkenylene; m, n and p are 0 or 1, but if m=0, n must=0; provided: that the sum of the carbon atoms in the $R^2$ and W groups must be greater than 4 but cannot exceed 21; that when X is mercapto, A and $A^1$ cannot be sulfinyl or sulfonyl; and that when A and $A^1$ are sulfinyl or sulfonyl, they must be in equal oxidation states.

40 Claims, No Drawings

DERIVATIVES OF A-30912D NUCLEUS

CROSS-REFERENCE TO RELATED APPLICATION

This application is a continuation-in-part of application Ser. No. 103,019, filed Dec. 13, 1979.

BACKGROUND OF THE INVENTION

This invention relates to novel semisynthetic antifungal compounds which are prepared by the acylation of the cyclic peptide nucleus produced by the enzymatic deacylation of antibiotic A30912 factor D.

Antibiotic A-30912 factor D is an antifungal cyclic peptide having the formula:

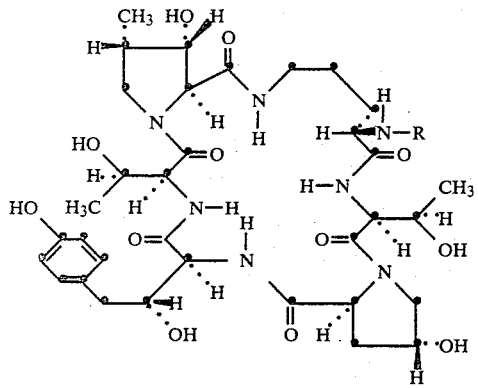

wherein R is the linoleoyl group

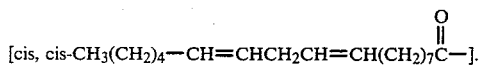

[cis, cis-$CH_3(CH_2)_4$—CH=$CHCH_2$CH=$CH(CH_2)_7\overset{O}{\overset{\|}{C}}$—].

Throughout this application, the cyclic peptide formulas, such as formula I, assume that the amino acids represented are in the L-configuration. The factor is isolated from the A30912 complex which contains other factors arbitrarily designated factors A, B, C, E, F, and G. The A-30912 complex and the individual factors A through G are disclosed by M. Hoehn and K. Michel in U.S. Pat. No. 4,024,245. Factor D has been found to be identical to antibiotic echinocandin D [see R. Traber et al., Helv. Chim. Acta, 62, 1252 (1979)] and to antibiotic SL 7810/F-III [see Belgium Pat. No. 834,289, Derwent Abstract 30159X].

Antibiotic A-30912 factor D is prepared by fermentation using one of several different organisms, namely: (a) Aspergillus rugulosus NRRL 8113 (see U.S. Pat. No. 4,024,245); (b) Aspergillus nidulans var. echinulatus A-32204, NRRL 3860, as described in Swiss Pat. No. 568,386; (c) Aspergillus rugulosus NRRL 8039 (see Belgian Patent No. 834,289); or (d) Aspergillus nidulans var. roseus NRRL 11440 (see co-pending application of L. Boeck and R. Kastner, METHOD OF PRODUCING THE A-30912 ANTIBIOTICS, Ser. No. 126,078, filed March 3, 1980, which is a continuation-in-part of application Ser. No. 46,744, filed June 8, 1979 (now abandoned), the entire disclosure of which is incorporated herein by reference.

A subculture of A. nidulans var. roseus has been deposited and made a part of the permanent culture collection of the Northern Regional Research Laboratory, U.S. Department of Agriculture, Agricultural Research Service, Peoria, Ill. 61604, from which it is available to the public under the number NRRL 11440.

When a strain of A. nidulans var. roseus NRRL 11440 is used to produce A-30912 factor D, a complex of factors is obtained which for convenience is called the A-42355 antibiotic complex. A-30912 factor A is the major factor of the A-42355 antibiotic complex, while factors B, D and H are minor factors. Examples 7, 8, and 9 herein, illustrate the preparation of the A-42355 complex and the isolation and purification of A-30912 factor D therefrom. A-30912 factor H, another factor in the A-30912 complex, is described in a co-pending application of Karl H. Michel entitled ANTIBIOTIC A-30912 FACTOR H, Ser. No. 117,739, filed Feb. 1, 1980, which is a continuation-in-part of application Ser. No. 46,875, filed June 8, 1979 (now abandoned).

In the antibiotic A-30912 factor D molecule (Formula I), the linoleoyl side chain (R) is attached at the cyclic peptide nucleus at the α-amino group of the ornithine residue. Surprisingly, it has been found that the linoleoyl side chain can be cleaved from the nucleus by an enzyme without affecting the chemical intregity of the nucleus. The enzyme employed to effect the deacylation reaction is produced by a microorganism of the family Actinoplanaceae, preferably the microorganism Actinoplanes utahensis NRRL 12052, or a variant thereof. To accomplish deacylation, antibiotic A30912 factor D is added to a culture of the microorganism and the culture is allowed to incubate with the substrate until the deacylation is substantially complete. The cyclic nucleus thereby obtained is separated from the fermentation broth by methods known in the art. Unlike antibiotic A-30912 factor D, the cyclic nucleus (lacking the linoleoyl side chain) is substantially devoid of antifungal activity.

The cyclic nucleus afforded by the afore-described enzymatic deacylation of antibiotic A-30912 factor D, is depicted in Formula II.

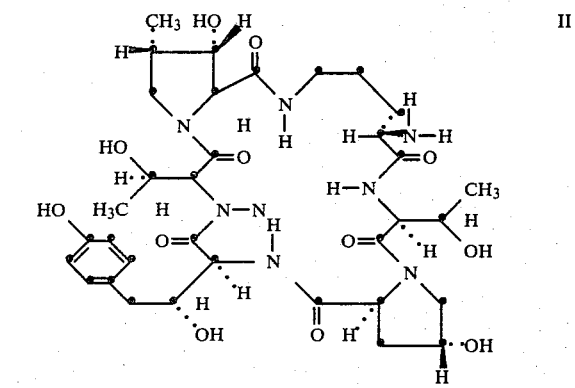

A-30912D nucleus has an empirical formula of $C_{34}H_{51}N_7O_{12}$ and a molecular weight of 749.83.

Removal of the side chain group affords a free primary α-amino group in the ornithine residue of the cyclic peptide. For convenience, the compound having the structure given in Formula II will be referred to herein as "A-30912D nucleus." As will be apparent to those skilled in the art, A-30912D nucleus can be obtained either in the form of the free amine or of the acid addition salt. Although any suitable acid addition salt may be employed, those which are non-toxic and pharmaceutically acceptable are preferred.

The method of preparing A-30912D nucleus from antibiotic A-30912 factor D by means of fermentation using *Actinoplanes utahensis* NRRL 12052 is described in the co-pending application of Bernard J. Abbott and David S. Fukuda entitled "A-30912D NUCLEUS", Docket No. X-5188, Ser. No. 103,268, filed Dec. 13, 1978, a continuation-in-part application of which is being filed herewith this even date, the full disclosure of which is incorporated herein by reference. Example 5 herein, illustrates the preparation of A-30912D nucleus by fermentation using antibiotic A-30912 factor D as the substrate and *Actinoplanes utahensis* NRRL 12052 as the microorganism.

The enzyme produced by *Actinoplanes utahensis* NRRL 12052 may be the same enzyme which has been used to deacylate penicillins (see Walter J. Kleinschmidt, Walter E. Wright, Frederick W. Kavanagh, and William M. Stark, U.S. Pat. No. 3,150,059, issued Sept. 22, 1964).

Cultures of representative species of Actinoplanaceae are available to the public from the Northern Regional Research Laboratory under the following accession numbers:

| | |
|---|---|
| Actinoplanes utahensis | NRRL 12052 |
| Actinoplanes missouriensis | NRRL 12053 |
| Actinoplanes sp. | NRRL 8122 |
| Actinoplanes sp. | NRRL 12065 |
| Streptosporangium roseum var. hollandensis | NRRL 12064 |

The effectiveness of any given strain of microorganism within the family Actinoplanaceae for carrying out the deacylation of this invention is determined by the following procedure. A suitable growth medium is inoculated with the microorganism. The culture is incubated at about 28° C. for two or three days on a rotary shaker. One of the substrate antibiotics is then added to the culture. The pH of the fermentation medium is maintained at about pH 6.5. The culture is monitored for activity using a *Candida albicans* assay. Loss of antibiotic activity is an indication that the microorganism produces the requisite enzyme for deacylation. This must be verified, however, using one of the following methods: (1) analysis by HPLC for presence of the intact nucleus; or (2) reacylation with an appropriate side chain (e.g. linoleoyl, stearoyl, or palmitoyl) to restore activity.

It is known that another antibiotic substance possesses the same nucleus as that of antibiotic A-30912 factor D. This substance, which differs from antibiotic A-30912 factor D in that a different acyl group is present in place of the linoleoyl group (R) in Formula I, is tetrahydro-A-30912 factor D (tetrahydroSL 7810/F-III; tetrahydro echinocandin D) described by R. Traber et al., *Helv. Chim. Acta*, 62 1252 (1979). Tetrahydro-A-30912 factor D is depicted in Formula I when R is stearoyl. Tetrahydro-A-30912 factor D can be prepared from antibiotic A-30912 factor D by catalytic hydrogenation using $PtO_2$ in ethanol under positive pressure. Tetrahydro-A-30912 factor D can be employed as a substrate in place of antibiotic A-30912 factor D for the enzymatic deacylation using the procedures herein described.

SUMMARY OF THE INVENTION

The invention sought to be patented comprehends novel compounds derived by acylating A-30912D nucleus (Formula II). The compounds of the present invention have the chemical structure depicted in Formula III:

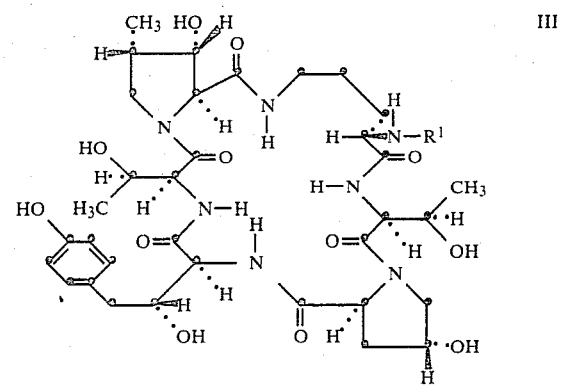

wherein $R^1$ is a group of the formula:

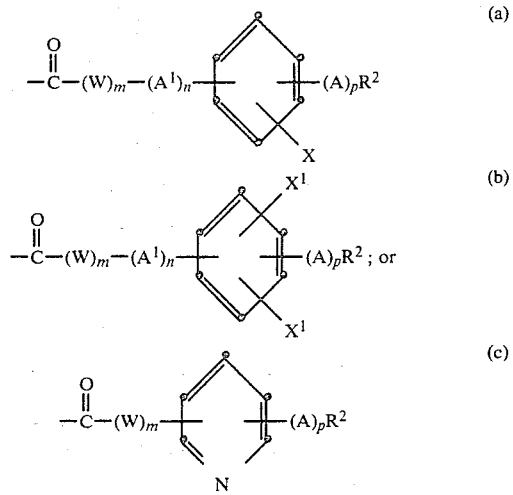

wherein A is divalent oxygen, sulfur, sulfinyl, or sulfonyl; $A^1$ is divalent oxygen, sulfur, sulfinyl, sulfonyl or —NH—; X is hydrogen, chloro, bromo, iodo, nitro, $C_1$-$C_3$ alkyl, hydroxy, $C_1$-$C_3$ alkoxy, mercapto, $C_1$-$C_3$ alkylthio, carbamyl or $C_1$-$C_3$ alkylcarbamyl; $X^1$ is chloro, bromo or iodo; $R^2$ is hydrogen, $C_1$-$C_{18}$ alkyl or $C_2$-$C_{18}$ alkenyl; W is $C_1$-$C_{10}$ alkylene or $C_2$-$C_{10}$ alkenylene; m, n and p are 0 or 1, but if m=0, n must=0; provided: that the sum of the carbon atoms in the $R^2$ and W groups must be greater than 4 but cannot exceed 21; that when X is mercapto, A and $A^1$ cannot be sulfinyl or sulfonyl; and that when A and $A^1$ are sulfinyl or sulfonyl, they must be in equal oxidation states.

A preferred subgroup of formula III compounds are those of group (a) wherein m and n=0, p=1, and $R^2$ is $C_5$-$C_{18}$ alkyl or $C_5$-$C_{18}$ alkenyl.

It will be recognized by those skilled in the art that in the substituted ring of the $R^1$ group, the

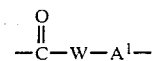

function and the —$AR^2$ function may be oriented on the benzene ring in the ortho, meta, or para position relative to each other. The para orientation for these groups is preferred. The substituent represented by X may be substituted at any available position of the benzene ring not occupied by these two groups.

As employed herein, the term "alkyl" or "alkenyl" comprehend both straight and branched hydrocarbon chains. By "alkenyl" is meant an unsaturated hydrocarbon group containing one, two, or three double bonds which may be either in the cis or trans configuration.

Illustrative $C_5$-$C_{18}$ alkyl radicals which are preferred for $R^2$ for the purposes of this invention are:

(a) —$(CH_2)_{n'}CH_3$ wherein n' is an integer from 4 to 17; and (b)

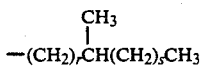

wherein r and s are, independently, an integer from 0 to 15, provided that r+s can be no greater than 15 or no less than 2.

Illustrative $C_5$-$C_{18}$ alkenyl radicals, which are preferred for $R^2$ for the purposes of this invention, are:

(a) —$(CH_2)_t$—CH=CH—$(CH_2)_{n''}$—$CH_3$ wherein t is an integer from 1 to 15, and n" is an integer from 0 to 15 provided that t+n" can be no greater than 15 or no less than 2; and (b) —$(CH_2)_v$—CH=CH—$(CH_2)_y$—CH=CH—$(CH_2)_zCH_3$ wherein v and z are, independently, an integer from 0 to 12 and y is an integer from 0 to 13 provided that v+y+z must be no greater than 13.

Illustrative $C_1$-$C_{10}$-alkylene radicals, which are preferred W groups for the purposes of this invention, are:

(a) —$(CH_2)_{n'''}$— wherein n''' is an integer from 1 to 10;

(b) methylene and ethylene; and (c)

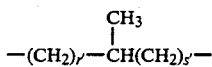

wherein r' and s' are, independently, integers from 0 to 8, provided that r'+s' can be no greater than 8 or no less than 1.

Illustrative $C_2$-$C_{10}$-alkenylene radicals, which are preferred W groups for the purposes of this invention, are:

(a) —$(CH_2)_{t'}$—CH=CH—$(CH_2)_{v'}$— wherein t' and v' are, independently, integers from 0 to 8, provided that t'+v' must be no greater than 8;

(b) —$(CH_2)_{x'}$—CH=CH—$(CH_2)_{y'}$—CH=CH—$(CH_2)_{z'}$— wherein x' and z' are, independently, integers from 0 to 5, and y' is an integer from 1 to 5, provided that x'+y'+z' must be no greater than 10.

Preferred embodiments of the compounds of Formula III are those wherein $R^1$ is:

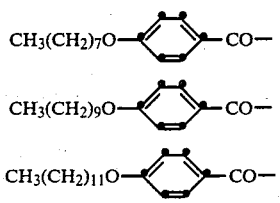

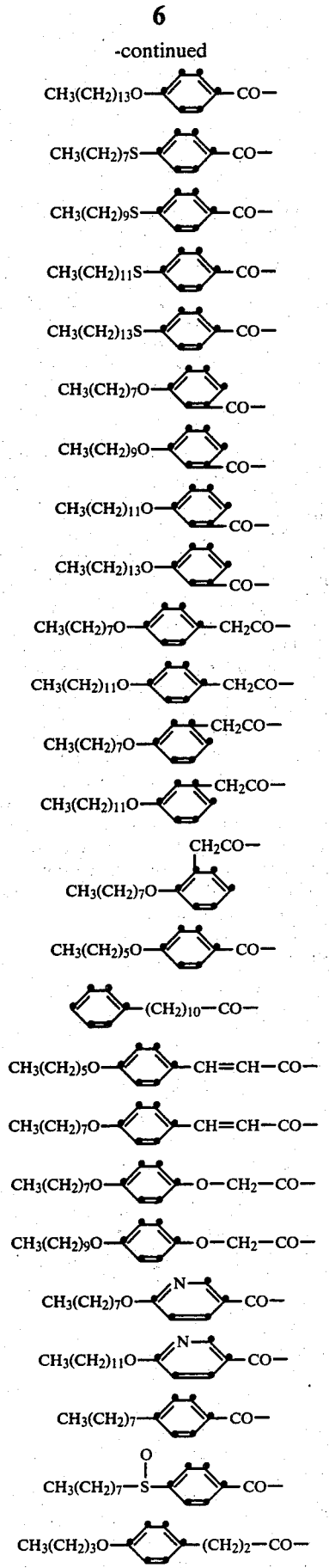

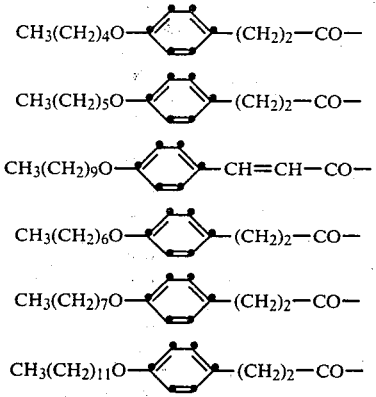

DETAILED DESCRIPTION OF THE INVENTION

The compounds of Formula III inhibit the growth of pathogenic fungi, and are useful, therefore, for controlling the growth of fungi on environmental surfaces (as an antiseptic) or in treating infections caused by fungi. In particular, the compounds are active against *Candida albicans* and are, thus, especially useful for treating candidosis. The activity of the compounds can be assessed in standard microbiological test procedures, such as in vitro in agar plate disc diffusion tests or in agar dilution tests, or in vivo in tests in mice infected with *C. albicans*. The compounds are also active against *Trichophyton mentagrophytes* (a dermatophytic organism), *Saccharomyces pastorianus*, and Neurospora crassa.

The compounds of Formula III are prepared by acylating A-30912D nucleus at the α-amino group of ornithine with the appropriate side chain using methods conventional in the art for forming an amide bond. The acylation is accomplished, in general, by reacting the nucleus with an activated derivative of the substituted compound of Formula IV (a), (b) or (c) corresponding to the desired acyl side chain group ($R^1$).

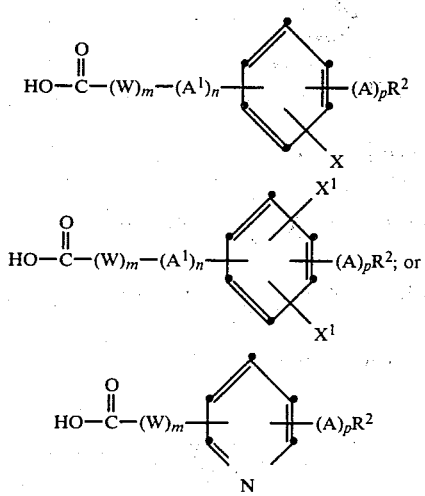

(A, $A^1$, W, m, n, p and $R^2$ have the meanings herein described supra.)

By the term "activated derivative" is meant a derivative which renders the carboxyl function of the acylating agent reactive to coupling with the primary amino group to form the amide bond which links the side chain to the nucleus. Suitable activated derivatives, their methods of preparation, and their methods of use as acylating agents for a primary amine will be recognized by those skilled in the art. Preferred activated derivatives are: (a) an acid halide (e.g. acid chloride), (b) an acid anhydride (e.g. an alkoxyformic acid anhydride or aryloxyformic acid anhydride) or (c) an activated ester (e.g. a 2,4,5-trichlorophenyl ester, an N-hydroxybenztriazole ester, or an N-hydroxysuccinimide ester). Other methods for activating the carboxyl function include reaction of the carboxylic acid with a carbonyldiimide (e.g. N,N'-dicyclohexylcarbodiimide or N,N'-diisopropylcarbodiimide) to give a reactive intermediate which, because of instability, is not isolated, the reaction with the primary amine being carried out in situ.

A preferred method for preparing the compounds of Formula III is by the active ester method. The use of the 2,4,5-trichlorophenyl ester of the desired side chain acid (Formula IV) as the acylating agent is most preferred. In this method, an excess amount of the active ester is reacted with the nucleus at room temperature in a non-reactive organic solvent such as dimethylformamide (DMF). The reaction time is not critical, although a time of about 24 to about 120 hours in preferred. At the conclusion of the reaction, the solvent is removed, and the residue is purified by chromatography, such as over silica gel using ethyl acetate-methanol (3:2, v/v) as the eluent, or by reversed phase HPLC using silica gel $C_{18}$ reversed phase resin as the stationary phase and a mixture of $H_2O/CH_3OH/CH_3CN$ as the solvent system.

The 2,4,5-trichlorophenyl esters are conveniently made by treating the side chain acid (Formula IV) with 2,4,5-trichlorophenol in the presence of a coupling agent, such as N,N'-dicyclohexylcarbodiimide. Other methods of preparation of the active esters will be apparent to those skilled in the art.

The substituted acids of Formula IV, and the activated derivatives thereof, are either known compounds or they can be made from known compounds by methods known in the art. The benzoic, phenylalkylcarboxylic, phenylalkenylcarboxylic, phenoxyalkylcarboxylic, phenoxyalkenylcarboxylic, phenylthioalkylcarboxylic, phenylthioalkenylcarboxylic, phenylsulfinylalkylcarboxylic, phenylsulfinylalkenylcarboxylic, phenylsulfonylalkylcarboxylic, phenylsulfonylalkenylcarboxylic, pyridinylcarboxylic, pyridinylalkylcarboxylic, and pyridinylalkenylcarboxylic acids of Formula IV are prepared by similar procedures. To illustrate these procedures, a discussion of the preparation of the benzoic acid subgroup is provided.

The alkoxybenzoic acids or alkenyloxybenzoic acids can be prepared conveniently from an appropriate hydroxybenzoic acid by reacting an appropriate alkyl or alkenyl halide with the disodium salt of the appropriate hydroxybenzoic acid. The (alkylthio)benzoic acids or the (alkenylthio)benzoic acids can be prepared conveniently by treating the appropriate substituted S-(4-carbomethoxyphenyl)dimethylthiocarbamate of the general formula $CH_3CO_2C_6H_3XS(CO)N(CH_3)_2$ with aqueous sodium hydroxide at 65°–85° C., then adding the appropriate alkyl or alkenyl bromide, and continuing heating for 2–4 hours. The substituted S-(4-carbomethoxyphenyl)dimethylthiocarbamates can be made from the appropriate hydroxybenzoic acids by the method of M. Newman and H. Kanes, *J. Org. Chem.*, 31, 3980 (1966).

When it is desired to prepare a compound of Formula III wherein A is sulfinyl or sulfonyl, the appropriate sulfoxide or sulfone derivative of the (alkenylthio)- or (alkylthio)benzoic acid (Formula IV) can be employed for acylation of the nucleus. The appropriate sulfoxides or sulfones can be made by oxidation of the corresponding thioether compound using conventional agents, such as m-chloroperbenzoic acid, t-butylhypochlorite, sodium metaperiodate, or hydrogen peroxide. If a double bond is present in the thioether, very mild conditions should be employed to avoid epoxidation. If equimolar amounts of reactants are taken, the product is a sulfoxide (A is sulfinyl), which is readily oxidized to the sulfone (A is sulfonyl) by an additional mole of the oxidizing agent. The hydroxybenzoic acids and substituted derivatives thereof used as starting material in the processes described herein are either known compounds or can be prepared by conventional methods which are known in the art.

When employed systemically, the dosage of the compounds of Formula III will vary according to the particular compound being employed, the severity and nature of the infection, and the physical condition of the subject being treated. Therapy should be initiated at low dosages, the dosage being increased until the desired antifungal effect is obtained. The compounds can be administered intravenously or intramuscularly by injection in the form of a sterile aqueous solution or suspension to which may be added, if desired, various conventional pharmaceutically acceptable preserving, buffering, solubilizing, or suspending agents. Other additives, such as saline or glucose may be added to make the solutions isotonic. The proportions and nature of such additives will be apparent to those skilled in the art.

When employed to treat vaginal candida infections, the compounds of Formula III can be administered in combination with pharmaceutically acceptable conventional excipients suitable for intravaginal use. Formulations adapted for intravaginal administration will be known to those skilled in the art.

The methods of making and using the compounds of the present invention are illustrated in the following examples:

EXAMPLE 1

A. Preparation of the Formula IV Acids

The preparation of the formula IV acids, such as, for example, the various alkoxybenzoic acids, (alkylthio)benzoic acids, alkoxyphenylacetic acids, alkoxyphenylpropanoic acids, alkoxycinnamic acids, alkoxyphenoxyacetic acids, and alkoxynicotinic acids, is typified by the preparation of the alkoxybenzoic acids and the (alkylthio)benzoic acids. The general procedure for the preparation of these acids is described in the following paragraphs.

The alkoxybenzoic acids are prepared according to the following general procedure:

p-Hydroxybenzoic acid is dissolved in 10% aqueous sodium hydroxide (two equivalents), and the resulting solution is added to dimethyl sulfoxide (DMSO) (200 ml). The alkyl bromide (one equivalent) is added to the solution at 65°–80° C. The solution is then stirred for two hours after which it is poured into a large volume (600 ml.) of water and acidified with hydrochloric acid. The alkoxybenzoic acid, which precipitates from the solution, is collected by filtration and crystallized from methanol.

The (alkylthio)benzoic acids are prepared according to the following general procedure:

To a suspension of sodium hydride (one equivalent, 50% dispersion in mineral oil) in dimethylformamide (DMF) (100 ml per 50 mmole), cooled to 0° C., is added slowly methyl p-hydroxybenzoate (one equivalent). The reaction mixture is stirred under a nitrogen atmosphere until the evolution of hydrogen ceases. To the solution of sodium 4carbomethoxyphenolate so produced, is added N,N-dimethylthiocarbamoyl chloride [(CH$_3$)$_2$N(CS)Cl] (one equivalent) in one portion. The resulting suspension is heated to 70° C. for 1–3 hours and then is poured into an aqueous solution (1%) of potassium hydroxide (large excess). The suspension is extracted twice with toluene-hexane (4:1 v/v). After drying over MgSO$_4$, the organic extracts are filtered and evaporated to an oil. The oil is purified by chromatography over silica gel using 2% methanol in methylene chloride to give O-(4-carbomethoxyphenyl)dimethylthiocarbamate [p-CH$_3$CO$_2$C$_6$H$_4$O(CS)N(CH$_3$)$_2$]. (mp 97°–120° C.). This product is heated under a nitrogen atmosphere at 220° C. for 30–60 min. to give S-(4-carbomethoxyphenyl)dimethylthiocarbamate [p-CH$_3$CO$_2$C$_6$H$_4$S(CO)N(CH$_3$)$_2$] which is crystallized from methanol. To S-(4-carbomethoxyphenyl)dimethylthiocarbamate, dissolved in DMSO, is added 2 equiv. of sodium hydroxide (10% aqueous). The mixture is heated at 65°–85° C., and the alkyl bromide (1 equiv.) is added. Heating is continued for 2–4 hours after which the mixture is poured into a large volume of water. Upon acidification, a precipitate forms, which is collected by filtration. The (alkylthio)benzoic acid is crystallized from methanol.

B. Preparation of Esters of the Formula IV Acids

The 2,4,5-trichlorophenyl esters of Formula IV acids, including the alkoxybenzoic acids and the (alkylthio)benzoic acids, are prepared according to the same general procedure. The following procedure is illustrative:

The alkoxybenzoic acid or (alkylthio)benzoic acid (1 mole), 2,4,5-trichlorophenol (1.1 mole), and N,N'-dicyclohexylcarbodiimide (1 mole) are dissolved in methylene chloride. The mixture is stirred at room temperature for 15–18 hours after it which it is filtered. The filtrate is evaporated to dryness under reduced pressure, and the residue is crystallized from acetonitrile-water. The product is dried under vacuum.

C. Preparation of the A-30912D Derivatives

The derivatives of A30912D nucleus are prepared in general from the 2,4,5-trichlorophenyl esters of Sect. B. according to the following procedure:

To A30912D nucleus, dissolved in DMF (10–50 ml.), is added the 2,4,5-trichlorophenyl ester of the alkoxybenzoic acid or the (alkylthio)benzoic acid (1:2 molar ratio). The reaction mixture is stirred for 15–18 hours after which it is taken to dryness to give a residue. The residue is washed (two times each) with a mixture of diethyl ether (50 ml) and methylene chloride (50 ml). The washings are discarded. The remaining residue is dissolved in ethyl acetate-methanol (3:2, v/v) and is chromatographed on a 100 ml. silica gel (Woelm, 70–150 ml.) column using the aforesaid solvent system as the eluent. The fractions from the chromatography are monitored by TLC on silica gel (Merck) using ethyl acetate-methanol (3:2, v/v) as the solvent system. Fractions containing the desired product are combined, and solvent is removed to give the product as a residue. The product may be analyzed by reverse phase HPLC as follows: In the alkoxy examples and the $C_{12}$ and $C_{14}$ alkylthio examples, the sample is dissolved in $H_2O/CH_3OH/CH_3CN$ (1:2:2 v/v). The sample solution (1 mg/ml) is injected into a ¼ in. by 12 in. stainless steel column packed with $C_{18}$ Micro Bondapak resin (Waters Associates, Milford, Mass.), and the column is eluted with a solvent system comprising $H_2O/CH_3OH/CH_3CN$ (1:2:2 v/v). In the $C_8$ and $C_{10}$ alkylthio examples, the solvent system is $H_2O/CH_3OH/CH_3CN$ (2:1:2 v/v). The elution is performed at a pressure of 1500 psi with a flow rate of 3 ml./minute using a Waters 600A pump (Waters Associates, Inc.) and chart speed of 0.2 in./minute. Eluent is monitored with a Varian Vari-Chrom UV detector at 230 nm. The products may also be analyzed by field desorption mass spectromety (FDMS).

Following the general method of this procedure, there are obtained the following compounds of Formula III:

$R^1$ p-(n-octylthio)benzoyl
p-(n-decylthio)benzoyl
p-(n-dodecylthio)benzoyl
p-(n-tetradecylthio)benzoyl
p-(n-octyl)benzoyl*
3-[p-(n-hexyloxy)phenyl]propanoyl
3-[p-(n-octyloxy)phenyl]propanoyl
3-[p-(n-dodecyloxy)phenyl]propanoyl
p-(n-hexyloxy)cinnamoyl
p-(n-octyloxy)cinnamoyl
[p-(n-octyloxy)phenyl]acetyl
[p-(n-dodecyloxy)phenyl]acetyl
3-[p-(n-pentyloxy)phenyl]propanoyl
3-[p-(n-heptyloxy)phenyl]propanoyl
p-(n-octyloxy)phenoxyacetyl
p-(n-decyloxy)phenoxyacetyl
6-(n-octyloxy)nicotinoyl
6-(n-dodecyloxy)nicotinoyl

* Best prepared by the acid chloride method, e.g. reacting p-(n-octyl)benzoyl chloride with nucleus in pyridine at room temperature under nitrogen for 24 hours.

EXAMPLE 2

The following procedure, which gives the preparation of the compound of formula III wherein $R^1$ is p-(n-octyloxy)benzoyl, also illustrates the method of preparation of the compounds of Formula III.

A. Preparation of p-(n-Octyloxy)benzoic Acid

A solution of p-hydroxybenzoic acid (19.2 g., 150 mmole) in 10% aqueous sodium hydroxide (120 ml.) is added to DMSO (480 ml.) previously heated to 80° C. n-Octyl bromide (28.95 g., 150 mmole) is added dropwise to the solution. The reaction mixture is stirred for 4 hours at room temperature after which it is poured into ice water (1200 ml.). Conc. hydrochloric acid (30 ml.) is added, and the mixture is allowed to stand until precipitation is complete. The precipitate is collected, dried, and crystallized from acetonitrile-water. m.p. 97°–99° C.

Analysis for $C_{15}H_{22}O_3$: Calculated: C, 71.97; H, 8.86. Found: C, 71.72; H, 9.10.

B. Preparation of the 2,4,5-Trichlorophenyl Ester of p-(n-Octyloxy)benzoic Acid p-(n-Octyloxy)benzoic acid (6.18 g., 24.7 mmole), 2,4,5-trichlorophenol (5.39 g., 27.2 mmole) and N,N'-dicyclohexylcarbodiimide (4.94 g., 24.7 mmole) are dissolved in methylene chloride (200 ml.). The mixture is stirred at room temperature for 18 hours and then is filtered. The filtrate is evaporated to give an oil, which is crystallized from $CH_3CN—H_2O$ to give the 2,4,5-trichlorophenyl ester of p-(n-octyloxy)benzoic acid.

NMR Analysis: $\delta 4.02$ (2H, t, J=3Hz), $\delta 7.0$ (1H, d, J=4Hz), 7.23 (s, 1H), 7.3 (s, 1H), 8.08 (d, 1H, J=4 Hz).

C. Acylation of A-30912D Nucleus

A-30912D nucleus (17.8 mmole) and the 2,4,5-trichlorophenyl ester of p-(n-octyloxy)benzoic acid (35.7 mmole) are dissolved in DMF (150 ml.). The solution is stirred at room temperature for 16–20 hours. Solvent is removed in vacuo and the residue is washed twice with diethyl ether and twice with methylene chloride. The washes are discarded. The washed residue is dissolved in 25% ethyl acetate-methanol (80 ml.) and is purified by high performance liquid chromatography using a "Prep LC/System 500" unit (Waters Associates, Inc., Milford, Mass.) employing silica gel as the stationary phase. The column is eluted stepwise with 20% to 40% methanol-ethyl acetate solvent systems. The fractions are analyzed by TLC using silica gel (Merck) and ethyl acetate-methanol (3:2 v/v) as the solvent system. Fractions devoid of A-30912D nucleus are pooled and lyophilized to give the p-(n-octyloxy)benzoyl derivative of A-30912D nucleus.

EXAMPLE 3

Following the procedure of Example 2 but substituting the appropriate alkyl bromide in Step A, the appropriate p-alkyloxybenzoic acid in Step B, and the appropriate p-alkyloxybenzoic acid 2,4,5-trichlorophenyl ester in Step C, there are obtained the following compounds of Formula III:

$R^1$ p-(n-decyloxy)benzoyl
p-(n-dodecyloxy)benzoyl
p-(n-tetradecyloxy)benzoyl
p-(n-hexyloxy)benzoyl

EXAMPLE 4

The following procedure illustrates the preparation of the compounds of Formula III wherein A is sulfonyl or sulfinyl.

A. Preparation of p-Alkylsulfonylbenzoic Acid 2,4,5-Trichlorophenyl Ester

To a solution of 2,4,5-trichlorophenyl p-(alkylthio)-benzoate (2 mmole) in methylene chloride (20 ml) cooled in an ice bath is added m-chloroperbenzoic acid (2.0 mmole). After allowing the reaction mixture to warm to room temperature (15 minutes), it is washed twice with 0.1 N sodium hydroxide (25 ml). The organic phase, after drying over anhyd. $Na_2SO_4$, is crystallized from acetonitrile. The product is reoxidized as described above using m-chloroperbenzoic acid in methylene chloride and a reaction time of 50 minutes. The product is purified as described above.

B. Acylation of A-30912D Nucleus

The acylation of A-30912D nucleus is carried out by the procedure described in Example 1, Step C, using the appropriate alkylsulfonylbenzoic acid 2,4,5-trichlorophenyl ester.

Illustrative p-alkylsulfonylbenzoyl derivatives of A-30912D nucleus are those of Formula III wherein $R^1$ is p-(n-octylsulfonyl)benzoyl, p-(n-decylsulfonyl)benzoyl, p-(n-dodecylsulfonyl)benzoyl, and p-(n-tetradecylsulfonyl)benzoyl.

When A is sulfinyl, the above conditions are modified accordingly. When the reaction gives a mixture of products, e.g. both sulfinyl and sulfonyl products, chromatographic separations may be required to obtain the desired sulfinyl product. The compound of Formula III wherein $R^1$ is p-(n-octylsulfinyl)benzoyl is an example of such a product.

EXAMPLE 5

Preparation of A30912D Nucleus

A. Fermentation of *Actinoplanes utahensis*

A stock culture of *Actinoplanes utahensis* NRRL 12052 is prepared and maintained on an agar slant. The medium used to prepare the slant is selected from one of the following:

| MEDIUM A | |
|---|---|
| Ingredient | Amount |
| Baby oatmeal | 60.0 g |
| Yeast | 2.5 g |
| K₂HPO₄ | 1.0 g |
| Czapek's mineral stock* | 5.0 ml |
| Agar | 25.0 g |
| Deionized water | q.s. to 1 liter |
| pH before autoclaving is about 5.9; adjust to pH 7.2 by addition of NaOH; after autoclaving, pH is about 6.7. | |

*Czapek's mineral stock has the following composition:

| Ingredient | Amount |
|---|---|
| FeSO₄ . 7H₂O (dissolved in 2 ml conc HCl) | 2 g |
| KCl | 100 g |
| MgSO₄ . 7H₂O | 100 g |
| Deionized water | q.s. to 1 liter |

| MEDIUM B | |
|---|---|
| Ingredient | Amount |
| Potato dextrin | 5.0 g |
| Yeast extract | 0.5 g |
| Enzymatic hydrolysate of casein* | 3.0 g |
| Beef extract | 0.5 g |
| Dextrose | 12.5 g |
| Corn starch | 5.0 g |
| Meat peptone | 5.0 g |
| Blackstrap molasses | 2.5 g |
| MgSO₄ . 7H₂O | 0.25 g |
| CaCO₃ | 1.0 g |
| Czapek's mineral stock | 2.0 ml |
| Agar | 20.0 g |
| Deionized water | q.s. to 1 liter |

*N-Z-Amine A, Humko Sheffield Chemical, Lyndhurst, N.J.

The slant is inoculated with *Actinoplanes utahensis* NRRL 12052, and the inoculated slant is incubated at 30° C. for about 8 to 10 days. About ½ of the slant growth is used to inoculate 50 ml of a vegetative medium having the following composition:

| Ingredient | Amount |
|---|---|
| Baby oatmeal | 20.0 g |
| Sucrose | 20.0 g |
| Yeast | 2.5 g |
| Distiller's Dried Grain* | 5.0 g |
| K₂HPO₄ | 1.0 g |
| Czapek's mineral stock | 5.0 ml |
| Deionized water | q.s. to 1 liter |
| adjust to pH 7.4 with NaOH; after autoclaving, pH is about 6.8. | |

*National Distillers Products Co., 99 Park Ave., New York, N.Y.

The inoculated vegetative medium is incubated in a 250-ml wide-mouth Erlenmeyer flask at 30° C. for about 72 hours on a shaker rotating through an arc two inches in diameter at 250 RPM.

This incubated vegetative medium may be used directly to inoculate a second-stage vegetative medium. Alternatively and preferably, it can be stored for later use by maintaining the culture in the vapor phase of liquid nitrogen. The culture is prepared for such storage in multiple small vials as follows: In each vial is placed 2 ml of incubated vegetative medium and 2 ml of a glycerol-lactose solution [see W. A. Dailey and C. E. Higgens, "Preservation and Storage of Microorganisms in the Gas Phase of Liquid Nitrogen," *Cryobiol* 10, 364–367 (1973) for details]. The prepared suspensions are stored in the vapor phase of liquid nitrogen.

A stored suspension (1 ml) thus prepared is used to inoculate 50 ml of a first-stage vegetative medium (having the composition earlier described). The inoculated first-stage vegetative medium is incubated as above-described.

In order to provide a larger volume of inoculum, 10 ml of the incubated first-stage vegetative medium is used to inoculate 400 ml of a second-stage vegetative medium having the same composition as the first-stage vegetative medium. The second-stage medium is incubated in a two-liter wide-mouth Erlenmeyer flask at 30° C. for about 48 hours on a shaker rotating through an arc two inches in diameter at 250 RPM.

Incubated second-stage vegetative medium (800 ml), prepared as above-described, is used to inoculate 100 liters of sterile production medium selected from one of the following:

| MEDIUM I | |
|---|---|
| Ingredient | Amount (g/L) |
| Peanut meal | 10.0 |
| Soluble meat peptone | 5.0 |
| Sucrose | 20.0 |
| KH₂PO₄ | 0.5 |
| K₂HPO₄ | 1.2 |
| MgSO₄ . 7H₂O | 0.25 |
| Tap water | q.s to 1 liter |
| The pH of the medium is about 6.9 after sterilization by autoclaving at 121° C. for 45 minutes at about 16–18 psi. | |

| MEDIUM II | |
|---|---|
| Ingredient | Amount (g/L) |
| Sucrose | 30.0 |
| Peptone | 5.0 |
| K₂HPO₄ | 1.0 |
| KCl | 0.5 |
| MgSO₄ . 7H₂O | 0.5 |
| FeSO₄ . 7H₂O | 0.002 |
| Deionized water | q.s. to 1 liter |
| Adjust to pH 7.0 with HCl; after autoclaving, pH is | |

| | |
|---|---|
| -continued | |
| about 7.0. | |

MEDIUM III

| Ingredient | Amount (g/L) |
|---|---|
| Glucose | 20.0 |
| $NH_4Cl$ | 3.0 |
| $Na_2SO_4$ | 2.0 |
| $ZnCl_2$ | 0.019 |
| $MgCl_2 \cdot 6H_2O$ | 0.304 |
| $FeCl_3 \cdot 6H_2O$ | 0.062 |
| $MnCl_2 \cdot 4H_2O$ | 0.035 |
| $CuCl_2 \cdot 2H_2O$ | 0.005 |
| $CaCO_3$ | 6.0 |
| $KH_2PO_4$* | 0.67 |
| Tap water | q.s. to 1 liter |

*Sterilized separately and added aseptically Final pH about 6.6.

The inoculated production medium is allowed to ferment in a 165-liter fermentation tank at a temperature of about 30° C. for about 42 hours. The fermentation medium is stirred with conventional agitators at about 200 RPM and aerated with sterile air to maintain the dissolved oxygen level about 30% of air saturation at atmospheric pressure.

B. Deacylation of A-30912 Factor D

A fermentation of *A. utahensis* is carried out as described in Sect. A, using production medium I. After the culture is incubated for about 48 hours, A-30912 factor D, dissolved in a small amount of methanol, is added to the fermentation medium.

Deacylation of A-30912 factor D is monitored by paper-disc assay against *Candida albicans* or *Neurospora crassa*. The fermentation is allowed to continue until deacylation is complete as indicated by disappearance of activity.

C. Isolation of A-30912D Nucleus

Whole fermentation broth, obtained as described in Sect. B is filtered. The mycelial cake is discarded. The clear filtrate thus obtained is passed through a column containing HP-20 resin (DIAION High Porous Polymer, HP-Series, Mitsubishi Chemical Industries Limited, Tokyo, Japan). The effluent thus obtained is discarded. The column is then washed with up to eight column volumes of deionized water at pH 6.5–7.5 to remove residual filtered broth. This wash water is discarded. The column is then eluted with a water:methanol (7:3) solution. Elution is monitored using the following procedure: Two aliquots are taken from each eluted fraction. One of the aliquots is concentrated to a small volume and is treated with an acid chloride such as myristoyl chloride. This product and the other (untreated) aliquot are assayed for activity against *Candida albicans*. If the untreated aliquot does not have activity and the acylated aliquot does have activity, the fraction contains A-30912D nucleus. The eluate containing A-30912D nucleus is concentrated under vacuum to a small volume and lyophilized to give crude nucleus.

D. Purification of A-30912D Nucleus by Reversed-Phase Liquid Chromatography

Crude A-30912D nucleus, obtained as described in Section C, is dissolved in water:acetonitrile:acetic:acid:pyridine (96:2:1:1). This solution is chromatographed on a column filled with Lichroprep RP-18, particle size 25–40 microns (MC/B Manufacturing Chemists, Inc. E/M, Cincinnati, OH). The column is part of a Chromatospac Prep 100 unit (Jobin Yvon, 16–18 Rue du Canal 91160 Longjumeau, France). The column is operated at a pressure of 90–100 psi, giving a flow rate of about 60 ml/minute, using the same solvent. Separation is monitored at 280 nm using a UV monitor (ISCO Absorption Monitor Model UA-5, Instrumentation Specialties Co., 4700 Superior Ave., Lincoln, Nebr. 68504) with an optical unit (ISCO Type 6).

On the basis of absorption at 280 nm, fractions containing A-30912D nucleus are combined, evaporated under vacuum and lyophilized to give purified A-30912D nucleus.

EXAMPLE 6

A-30912D nucleus is prepared and purified by the method of Example 1 except that tetrahydro-A-30912D is used as the substrate.

EXAMPLE 7

Preparation of the A-42355 Antibiotic Complex

A. Shake-Flask Fermentation

A culture of *Aspergillus nidulans* var. roseus NRRL 11440 is prepared and maintained on an agar slant prepared with medium having the following composition:

| Ingredient | Amount |
|---|---|
| Glucose | 5 g |
| Yeast extract | 2 g |
| $CaCO_3$ | 3 g |
| Vegetable juice* | 200 ml |
| Agar** | 20 g |
| Deionized water | q.s. to 1 liter |

(initial pH 6.1)
*V-8 Juice, Campbell Soup Co., Camden, N.J.
**Meer Corp.

The slant is inoculated with *Aspergillus nidulans* var. roseus NRRL 11440, and the inoculated slant is incubated at 25° C. for about seven days. The mature slant culture is covered with water and scraped with a sterile loop to loosen the spores. The resulting suspension is further suspended in 10 ml of sterile deionized water.

One ml of the suspended slant growth is used to inoculated 55 ml of vegetative medium in a 250-ml flask. The vegetative medium has the following composition:

| Ingredient | Amount |
|---|---|
| Sucrose | 25 g |
| Blackstrap molasses | 36 g |
| Corn-steep liquor | 6 g |
| Malt extract | 10 g |
| $K_2HPO_4$ | 2 g |
| Enzymatic hydrolysate of casein* | 10 g |
| Tap water | 1100 ml |

(initial pH 6.5–6.7)
*N-Z-Case, Humko Sheffield Chemical, Lyndhurst, N.J.

The inoculated vegetative medium is incubated at 25° C. for 48 hours at 250 rpm on a rotary-type shaker. After 24 hours, the medium is homogenized for one minute at low speed in a blender (Waring type) and then returned to incubation for the remaining 24 hours. Alternatively, the inoculated vegetative medium can be incubated for 48 hours and then homogenized for 15 seconds at low speed.

This incubated vegetative medium may be used to inoculate shake-flask fermentation culture medium or to inoculate a second-stage vegetative medium. Alternatively, it can be stored for later use by maintaining the culture in the vapor phase of liquid nitrogen. The culture is prepared for such storage in multiple small vials as follows: The vegetative cultures are mixed volume/volume with a suspending solution having the following composition:

| Ingredient | Amount |
| --- | --- |
| Glycerol | 20 ml |
| Lactose | 10 g |
| Deionized water | q.s. to 100 ml |

The prepared suspensions are distributed in small sterile screw-cap tubes (4 ml per tube). These tubes are stored in the vapor phase of liquid nitrogen.

A stored suspension thus prepared can be used to inoculate either agar slants or liquid seed media. Slants are incubated at 25° C. in the light for 7 days.

B. Tank Fermentation

In order to provide a larger volume of inoculum, 10 ml of incubated first-stage vegetative culture is used to inoculate 400 ml of a second-stage vegetative growth medium having the same composition as that of the vegetative medium. The second-stage medium is incubated in a two-liter wide-mouth Erlenmeyer flask at 25° C. for 24 hours on a shaker rotating through an arc two inches in diameter at 250 rpm.

Incubated second-stage medium (800 ml), prepared as above described, is used to inoculate 100 liters of sterile production medium selected from one of the following:

| MEDIUM IV | |
| --- | --- |
| Ingredient | Amount |
| $ZnSO_4 \cdot 7H_2O$ | 0.00455 g/L |
| Soluble meat peptone* | 30.5 g/L |
| Soybean meal | 15.5 g/L |
| Tapioca dextrin** | 2.0 g/L |
| Blackstrap molasses | 10.5 g/L |
| Enzymatic hydrolysate of casein*** | 8.5 g/L |
| $Na_2HPO_4$ | 4.5 g/L |
| $MgSO_4 \cdot 7H_2O$ | 5.5 g/L |
| $FeSO_4 \cdot 7H_2O$ | 0.1 g/L |
| Cottonseed oil | 40.0 ml |
| (Antifoam)**** | 1.0 ml |
| Tap water | 1000.0 ml |

(initial pH 6.8–7.0)
*O.M. Peptone, Amber Laboratories, Juneau, Wisc.
**Stadex 11, A.E. Staley Co., Decatur, Ill.
***N-Z-Amine A, Humko Sheffield Chemical, Lyndhurst, N.J.
****P2000, Dow Corning, Midland, Michigan

| MEDIUM V | |
| --- | --- |
| Ingredient | Amount |
| Glucose | 2.5% |
| Starch | 1.0% |
| Soluble meat peptone* | 1.0% |
| Blackstrap molasses | 1.0% |
| $CaCO_3$ | 0.2% |
| $MgSO_4 \cdot 7H_2O$ | 0.05% |
| Enzymatic hydrolysate of casein** | 0.4% |
| (Antifoam)*** | 0.02% |
| Tap water | q.s. to volume |

*O.M. Peptone
**N-Z-Amine A
***Antifoam "A", Dow Corning

The inoculated production medium is allowed to ferment in a 165-liter fermentation tank at a temperature of 25° C. for about 7 days. The fermentation medium is aerated with sterile air, maintaining the dissolved oxygen level above approximately 50 percent of air saturation.

C. Third-Stage Vegetative Medium

Whenever the fermentation is carried out in tanks larger than those used for 100-liter fermentation, it is recommended that a third-stage vegetative culture be used to seed the larger tank. A preferred third-stage vegetative medium has the following composition:

| Ingredient | Amount |
| --- | --- |
| Sucrose | 25 g |
| Blackstrap molasses | 25 g |
| Corn-steep liquor | 6 g |
| Enzymatic hydrolysate of casein* | 10 g |
| Malt extract | 10 g |
| $K_2HPO_4$ | 2 g |
| Tap water | 1000 ml |

(initial pH 6.1)
*N-Z-Case

EXAMPLE 8

Separation of the A-42355 Antibiotic Complex

Whole fermentation broth (4127 liters), obtained by the method described in Example 7 using production medium V, is stirred thoroughly with methanol (4280 liters) for one hour and then is filtered, using a filter aid (Hyflo Super-cel, a diatomaceous earth, Johns-Manville Products Corp.). The pH of the filtrate is adjusted to pH 4.0 by the addition of 5 N HCl. The acidified filtrate is extracted twice with equal volumes of chloroform. The chloroform extracts are combined and concentrated under vacuum to a volume of about 20 liters. This concentrate is added to about 200 liters of diethyl ether to precipitate the A-42355 complex. The precipitate is separated by filtration to give 2775 g of the A-42355 complex as a gray-white powder.

EXAMPLE 9

Isolation of A-30912 Factor D

Concentrated chloroform extracts from two fermentation runs (3800 L and 4007 L) obtained by the method described in Example 6 are combined and chromatographed on a silica-gel column (Grace, grade 62). The column is washed with chloroform and then is eluted with acetonitrile and acetonitrile:water (98:2). Fractions having a volume of approximately 200 L are collected and analyzed for biological activity by paper-disc assay on agar seeded with *Candida albicans*. Fractions having activity (850 L) are combined and concentrated under vacuum. The concentrated solution (0.7 L) is added to diethyl ether (10 volumes) to precipitate the factor D-enriched A-42355 complex. This precipitate is removed by filtration and dried to give 32 g, of factor D-enriched A-42355 complex as a gray powder.

Factor D-enriched A-42355 complex thus obtained (1.0 g,) is dissolved in 5 ml. of methanol:water:acetonitrile (7:2:1). This solution is filtered and introduced onto a silica-gel column (3.7-cm I.D.×30-cm Michel-Miller Column) through a loop with the aid of a valve system. The column is packed with LP-1/$C_{18}$ silica-gel reversed-phase resin (10–20 microns), prepared as described in Example 10. Packing is accomplished in methanol:water:acetonitrile (7:2:1) by the slurry-packing procedure described in Example 11. The solvent is moved through the column at a flow rate of 8 ml/min at ca. 45 psi using an F.M.I. pump with valveless piston design. One fraction is collected every 2 minutes. Elution of the antibiotic is monitored at 280 nm by using a UV monitor (ISCO Model UA-5) with an optical unit (ISCO Type 6). Fractions 96–108 are combined and concentrated under vacuum to give an oil. This oil is dissolved in a small volume of tert-butanol and lyophilized to give 89 mg, of A-30912 factor D.

The individual A-30912 factors can be identified by the use of thin-layer chromatography (TLC). The $R_f$ values of A-30912 factors A–G, using silica gel (Merck, Darmstadt) TLC, a benzene:methanol (7:3) solvent system, and *Candida albicans* bioautography are given in Table I.

TABLE I

| A-30912 Factor | $R_f$ Value |
|---|---|
| A | 0.35 |
| B | 0.45 |
| C | 0.54 |
| D | 0.59 |
| E | 0.27 |
| F | 0.18 |
| G | 0.13 |

The approximate $R_f$ values of A-30912 factors A, B, C, D, and H in different solvent systems, using silica gel TLC (Merck-Darmstadt silica gel #60 plates, 20×20 cm) and *Candida albicans* bioautography, are given in Table II.

TABLE II

| A-30912 Factor | $R_f$ Values - Solvent Systems | | | |
|---|---|---|---|---|
| | a | b | c | d |
| Factor A | 0.28 | 0.14 | 0.28 | 0.43 |
| Factor B | 0.39 | 0.21 | 0.42 | 0.47 |
| Factor C | 0.46 | 0.31 | 0.51 | 0.58 |
| Factor D | 0.50 | 0.38 | 0.57 | 0.61 |
| Factor H | 0.42 | 0.27 | 0.36 | 0.53 |

Solvent Systems
a: ethyl acetate:methanol (3:2)
b: ethyl acetate:methanol (7:3)
c: acetonitrile:water (95:5)
d: ethyl acetate:ethanol:acetic acid (40:60:0.25)

A-30912 factors A, B, D and H can also be indentified by analytical HPLPLC using the following conditions:

| | |
|---|---|
| Column: | glass, 0.8 × 15.0 cm |
| Packing: | Nucleosil ® 10-$C_{18}$ (Machery-Nagel and Company); packed using slurry-packing procedure of Example 8 |
| Solvent: | methanol:water:acetonitrile (7:2:1) |
| Sample Volume: | 8 mcl |
| Sample Size: | 8 mcg |
| Column Temperature: | ambient |
| Flow Rate: | 1.8 ml/min |
| Pressure: | ca. 200 psi |
| Detector: | UV at 222 nm (ISCO Model 1800 Variable Wavelength UV-Visible Absorbance Monitor) |
| Pump: | LDC Duplex Minipump |
| Injection: | loop injection |

The approximate retention times for A-30912 factors A, B, D, and H under these conditions are summarized in Table III.

TABLE III

| A-30912 Factor | Retention Time (seconds) |
|---|---|
| A | 792 |
| B | 870 |
| H | 990 |
| D | 1,140 |

EXAMPLE 10

Preparation of Silica Gel/$C_{18}$ Reversed Phase Resin

Step 1: Hydrolysis

LP-1 silica gel (1000 g from Quantum Corp., now Whatman) is added to a mixture of concentrated sulfuric acid (1650 ml) and concentrated nitric acid (1650 ml) in a 5-L round-bottom flask and shaken for proper suspension. The mixture is heated on a steam bath overnight (16 hours) with a water-jacketed condenser attached to the flask.

The mixture is cooled in an ice bath and carefully filtered using a sintered-glass funnel. The silica gel is washed with deionized water until the pH is neutral. The silica gel is then washed with acetone (4 L) and dried under vacuum at 100° C. for 2 days.

Step 2: First Silylation

The dry silica gel from Step 1 is transferred to a round-bottom flask and suspended in toluene (3.5 L). The flask is heated on a steam bath for 2 hours to azeotrope off some residual water. Octadecyltrichlorosilane (321 ml, Aldrich Chemical Company) is added, and the reaction mixture is refluxed overnight (16 hours) with slow mechanical stirring at about 60° C. Care is taken so that the stirrer does not reach near the bottom of the flask in order to prevent grinding the silica gel particles.

The mixture is allowed to cool. The silanized silica gel is collected, washed with toluene (3 L) and acetone (3 L), and then air-dried overnight (16–20 hours). The dried silica gel is suspended in 3.5 L of acetonitrile:water (1:1) in a 5-L flask, stirred carefully at room temperature for 2 hours, filtered, washed with acetone (3 L) and air-dried overnight.

Step 3: Second Silylation

The procedure from the first silylation is repeated using 200 ml of octadecyltrichlorosilane. The suspension is refluxed at 60° C. for 2 hours while stirring carefully. The final product is recovered by filtration, washed with toluene (3 L) and methanol (6 L), and then dried under vacuum at 50° C. overnight (16–20 hours).

EXAMPLE 11

Slurry Packing Procedure for Michel-Miller Columns

General Information

This procedure is employed for packing silica gel $C_{18}$ reversed phase resin such as that prepared by the method of Example 10. Generally, a pressure of less than 200 psi and flow rates between 5–40 ml/minute are required for this slurry packing technique; this is dependent on column volume and size. Packing pressure should exceed the pressure used during actual separation by 30–50 psi; this will assure no further compression of the adsorbent during separation runs.

21

A sudden decrease in pressure may cause cracks or channels to form in the packing material, which would greatly reduce column efficiency. Therefore, it is important to let the pressure drop slowly to zero whenever the pump is turned off.

The approximate volume of columns (Ace Glass Cat. No., unpacked) are No. 5795-04, 12 ml; No. 5795-10, 110 ml; No. 5795-16, 300 ml; No. 5795-24, 635 ml; and No. 5796-34, 34 ml.

The time required to pack a glass column will vary from minutes to several hours depending on column size and the experience of the scientist.

Example:
1. Connect glass column to a reservoir column via coupling (volume of reservoir column should be twice that of the column). Place both columns in vertical positions (reservoir column above).
2. Weigh out packing material (ca. 100 g for 200 ml column).
3. Add ca. five volumes of solvent to packing material; use a mixture of 70-80% methanol and 20-30% water.
4. Shake well until all particles are wetted, let stand overnight or longer to assure complete soaking of particles by solvent. Decant supernatant.
5. Slurry the resin with sufficient solvent to fill reservoir column. Pour swiftly into reservoir. The column must be pre-filled with the same solvent and the reservoir column should be partly filled with solvent before slurry is poured. The use of larger slurry volumes may also provide good results; however, this will require (a) larger reservoir or (b) multiple reservoir fillings during the packing procedure.
6. Close reservoir with the Teflon plug beneath the column (see FIG. 1 of U.S. Pat. No. 4,131,547, plug No. 3); connect to pump; and immediately start pumping solvent through system at maximum flow rate if Ace Cat. No. 13265-25 Pump or similar solvent-delivery system is used (ca. 20 ml/minute).
7. Continue until column is completely filled with adsorbent. Pressure should not exceed maximum tolerance of column during this operation (ca. 200 psi for large columns and 300 psi for analytical columns). In most cases, pressures less than 200 psi will be sufficient.
8. Should pressure exceed maximum values, reduce flow-rate; pressure will drop.
9. After column has been filled with adsorbent, turn off pump; let pressure drop to zero; disconnect reservoir; replace reservoir with a pre-column; fill pre-column with solvent and small amount of adsorbent; and pump at maximum pressure until column is completely packed. For additional information, see general procedure. Always allow pressure to decrease slowly after turning off pump—this will prevent formation of any cracks or channels in the packing material.
10. Relieve pressure and disconnect precolumn carefully. With small spatula remove a few mm (2-4) of packing from top of column; place 1 or 2 filter(s) in top of column; gently depress to top of packing material, and place Teflon plug on top of column until seal is confirmed. Connect column to pump, put pressure on (usually less than 200 psi) and observe through glass wall on top of column if resin is packing any further. If packing material should continue to settle (this may be the case with larger columns), some dead space or channelling will appear and step 9 should be repeated.

EXAMPLE 12

Preparation of Tetrahydro-A-30912D

A-30912 factor D is dissolved in ethanol. $PtO_2$ in absolute ethanol is reduced to form Pt, which in turn is used to reduce the A-30912 factor D catalytically, using hydrogenation under positive pressure until the reaction is complete (about 2-3 hours). The reaction mixture is filtered and concentrated under vacuum. The residue is dissolved in a small amount of tert-butanol and lyophilized to give tetrahydro-A-30912D.

What is claimed is:

1. A compound of the formula:

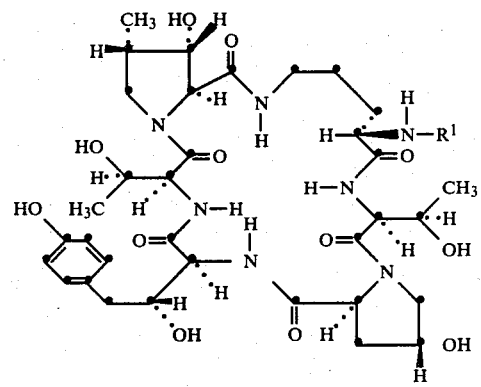

wherein $R^1$ is a group of the formula:

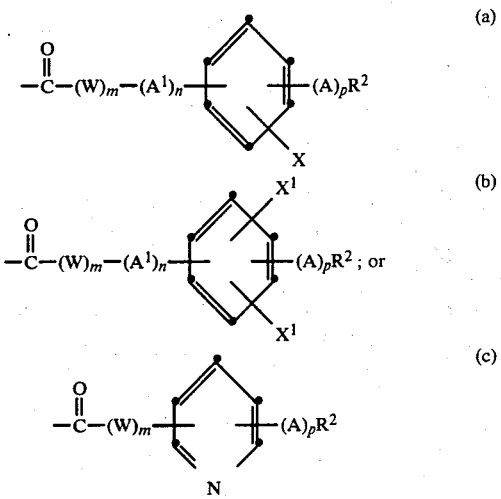

wherein A is divalent oxygen, sulfur, sulfinyl, or sulfonyl; $A^1$ is divalent oxygen, sulfur, sulfinyl, sulfonyl or —NH—; X is hydrogen, chloro, bromo, iodo, nitro, $C_1$-$C_3$ alkyl, hydroxy, $C_1$-$C_3$ alkoxy, mercapto, $C_1$-$C_3$ alkylthio, carbamyl or $C_1$-$C_3$ alkylcarbamyl; $X^1$ is chloro, bromo or iodo; $R^2$ is hydrogen $C_1$-$C_{18}$ alkyl or $C_2$-$C_{18}$ alkenyl; W is $C_1$-$C_{10}$ alkylene or $C_2$-$C_{10}$ alkenylene; m, n and p are 0 or 1, but if m=0, n must=0; provided: that the sum of the carbon atoms in the $R^2$ and W groups must be greater than 4 but cannot exceed 21; that when X is mercapto, A and $A^1$ cannot be sulfinyl or sulfonyl and that when A and $A^1$ are sulfinyl or sulfonyl, they must be in equal oxidation states.

2. A compound of claim 1 wherein $R^1$ is a substituted benzoyl group of the formula:

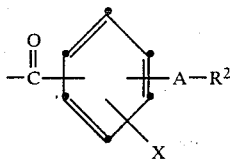

wherein A is divalent oxygen, sulfur, sulfinyl, or sulfonyl, X is hydrogen, chloro, bromo, iodo, nitro, $C_1$–$C_3$alkyl, hydroxy, $C_1$–$C_3$alkoxy, mercapto, $C_1$–$C_3$alkylthio, carbamyl, or $C_1$–$C_3$alkylcarbamyl; and $R^2$ is $C_5$–$C_{18}$alkyl or $C_5$–$C_{18}$alkenyl.

3. A compound as defined in claim 1 or 2 wherein A is oxygen.

4. A compound as defined in claim 3 wherein X is hydrogen and $R^2$ is straight chain $C_5$–$C_{18}$alkyl.

5. The compound as defined in claim 2 wherein $R^1$ is p-(n-octyloxy)benzoyl.

6. The compound as defined in claim 2 wherein $R^1$ is p-(n-decyloxy)benzoyl.

7. The compound as defined in claim 2 wherein $R^1$ is p-(n-dodecyloxy)benzoyl.

8. The compound as defined in claim 2 wherein $R^1$ is p-(n-tetradecyloxy)benzoyl.

9. The compound as defined in claim 2 wherein $R^1$ is p-(n-hexyloxy)benzoyl.

10. A compound as defined in claim 1 or 2 wherein A is sulfur.

11. The compound as defined in claim 10 wherein X is hydrogen and $R^2$ is straight chain $C_5$–$C_{18}$alkyl.

12. The compound as defined in claim 2 wherein $R^1$ is p-(n-octylthio)benzoyl.

13. The compound as defined in claim 2 wherein $R^1$ is p-(n-decylthio)benzoyl.

14. The compound as defined in claim 2 wherein $R^1$ is p-(n-dodecylthio)benzoyl.

15. The compound as defined in claim 2 wherein $R^1$ is p-(n-tetradecylthio)benzoyl.

16. A compound as defined in claim 1 or 2 wherein A is sulfonyl.

17. A compound as defined in claim 16 wherein X is hydrogen and $R^2$ is straight chain $C_5$–$C_{18}$ alkyl.

18. A compound as defined in claim 2 wherein $R^1$ is p-(n-octylsulfonyl)benzoyl.

19. A compound as defined in claim 2 wherein $R^1$ is p-(n-decylsulfonyl)benzoyl.

20. A compound as defined in claim 2 wherein $R^1$ is p-(n-dodecylsulfonyl)benzoyl.

21. A compound as defined in claim 2 wherein $R^1$ is p-(n-tetradecylsulfonyl)benzoyl.

22. A compound of claim 1 wherein $R^1$ is formula (a), X is hydrogen, and m, n and p are zero.

23. The compound of claim 22 wherein $R^1$ is p-(n-octyl)benzoyl.

24. A compound of claim 1 wherein $R^1$ is formula (a), X is hydrogen, A is oxygen, and n is zero.

25. The compound of claim 24 wherein $R^1$ is 3-[p-(n-hexyloxy)phenyl]propanoyl.

26. The compound of claim 24 wherein $R^1$ is 3-[p-(n-octyloxy)phenyl]propanoyl.

27. The compound of claim 24 wherein $R^1$ is 3-[p-(n-dodecyloxy)phenyl]propanoyl.

28. The compound of claim 24 wherein $R^1$ is p-(n-hexyloxy)cinnamoyl.

29. The compound of claim 24 wherein $R^1$ is p-(n-octyloxy)cinnamoyl.

30. The compound of claim 24 wherein $R^1$ is [p-(n-octyloxy)phenyl]acetyl.

31. The compound of claim 24 wherein $R^1$ is [p-(n-dodecyloxy)phenyl]acetyl.

32. The compound of claim 24 wherein $R^1$ is 3-[p-(n-pentyloxy)phenyl]propanoyl.

33. The compound of claim 24 wherein $R^1$ is 3-[p-(n-heptyloxy)phenyl]propanoyl.

34. A compound of claim 1 wherein $R^1$ is formula (a), X is hydrogen, and both A and $A^1$ are oxygen.

35. The compound of claim 34 wherein $R^1$ is p-(n-octyloxy)phenoxyacetyl.

36. The compound of claim 34 wherein $R^1$ is p-(n-decyloxy)phenoxyacetyl.

37. A compound of claim 1 wherein $R^1$ is formula (c).

38. The compound of claim 37 wherein $R^1$ is 6-(n-octyloxy)nicotinoyl.

39. The compound of claim 37 wherein $R^1$ is 6-(n-dodecyloxy)nicotinoyl.

40. The compound of claim 24 wherein $R^1$ is p-(n-decyloxy)cinnamoyl.

* * * * *